United States Patent [19]

Hakamatsuka et al.

[11] Patent Number: 5,318,779
[45] Date of Patent: Jun. 7, 1994

[54] DRUG-IMPREGNATED CERAMIC

[75] Inventors: Yasuharu Hakamatsuka; Hiroyuki Irie, both of Hachioji, Japan

[73] Assignee: Olympus Optical Co., Ltd., Tokyo, Japan

[21] Appl. No.: 494,849

[22] Filed: Mar. 15, 1990

Related U.S. Application Data

[63] Continuation of Ser. No. 300,351, Jan. 23, 1989, abandoned.

[30] Foreign Application Priority Data

Jan. 30, 1988 [JP]  Japan ................................ 63-20014

[51] Int. Cl.$^5$ ................................................ A61K 9/52
[52] U.S. Cl. .................................... 424/426; 424/422; 424/463; 424/473
[58] Field of Search ............... 424/423, 433, 426, 473, 424/422, 463; 428/403, 404; 128/92

[56] References Cited

U.S. PATENT DOCUMENTS 4,737,411  4/1988  Graves et al. ........................ 428/404
4,778,471  10/1988  Bajpai ..................................... 128/92

FOREIGN PATENT DOCUMENTS 59-101145  6/1984  Japan .
59-131346  7/1984  Japan .

*Primary Examiner*—Thurman K. Page
*Assistant Examiner*—Leon Horne
*Attorney, Agent, or Firm*—Frishauf, Holtz, Goodman & Woodward

[57] ABSTRACT

A drug-impregnated ceramic to be embedded in a living body is disclosed, and includes a porous ceramic having pores with a pore size of 10 to 300 μm, a drug impregnating the porous ceramic via the pores, and a surface layer for controlling the release of the drug. The surface layer is formed to cover at least a portion of the outer surface of the porous ceramic and has a porosity lower than that of the porous ceramic.

19 Claims, 1 Drawing Sheet

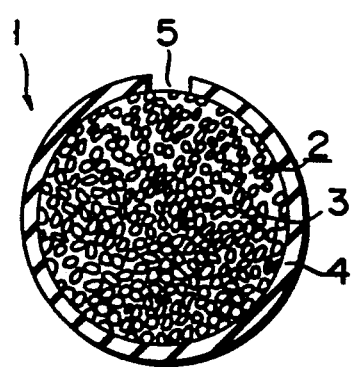
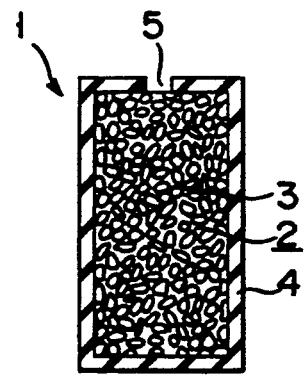
F I G. 1    F I G. 2
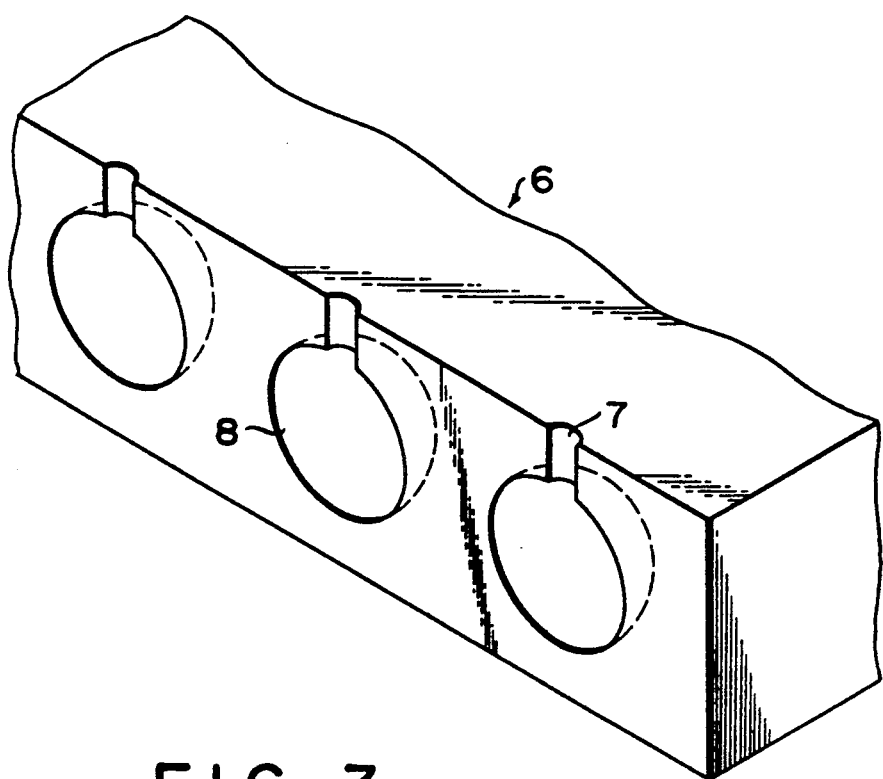
F I G. 3

DRUG-IMPREGNATED CERAMIC

This application is a continuation of application Ser. No. 07/300,351, filed Jan. 23, 1989 and now abandoned.

BACKGROUND OF THE INVENTION

1. Field of the Invention

The present invention relates to a drug-impregnated ceramic to be embedded in an affected region of a living body in order to treat myelitis, a malignant tumor, and the like.

2. Description of the Related Art

According to a conventional method of treating myelitis, an antibiotic is administered through a vinyl tube inserted into an affected region. Using this method, however, makes it difficult to administer the antibiotic throughout all of the affected region over an extended time period, and patient is obliged to suffer from large stress or invasion.

With the aim of solving this problem, Japanese Patent Disclosure (Kokai) No. 59-101145 discloses a drug-impregnated porous ceramic having in its surface layer 10- to 500-$\mu$m diameter pores the ceramic itself being composed of one or more members selected from a group consisting of calcium phosphate, alumina, zirconia and silicon nitride.

When such a drug-impregnated porous substance is embedded in an affected region, the drug exudes into the region over an extended time period, resulting in the drug being continuously administered to achieve the desired treatment. In addition, since the above ceramic is not harmful to a living body, no serious adverse effects will occur even is the ceramic remains within the body.

Nevertheless, the above conventional drug-impregnated ceramic does have the following drawbacks.

The release period and concentration of a drug impregnated in the porous ceramic into a living body are controlled by adjusting a pore size. Since the pores communicate with the outer surface of the ceramic, however, the release concentration of the drug is inevitably high immediately after the ceramic is embedded in an affected part. For this reason, since a large amount of the drug is released immediately after the ceramic is embedded, it is difficult to maintain a constant release concentration throughout an release period from immediately after the ceramic is embedded. Also, the drug release period itself is shortened.

In addition, since the above porous ceramic is not decomposed in a living body, drug components impregnated deep in the pores often remains therein unreleased. The unreleased drug is not available for treatment.

Furthermore, although the porous ceramic is harmless to a living body, it is not decomposed in a living body but remains therein as an alien substance, thereby producing a lump in an affected part. Therefore, in the case that bone formation need not be performed in the affected part, the part must be cut open to remove the ceramic after a drug is released. As a result, the patient may suffer physically, mentally, and even economically.

SUMMARY OF THE INVENTION

It is a first object of the present invention to provide a drug-impregnated ceramic which, immediately after it is embedded in a living body, can release a drug impregnated therein at a substantially constant concentration.

It is a second object of the present invention to provide a drug-impregnated ceramic which can reliably release all the drug components impregnated therein and does not require to be removed from a living body even after all of the drug components have been released.

The above first object of the present invention is achieved by a drug-impregnated ceramic to be embedded in a living body, and comprising:

a porous ceramic having pores with a pore size of 10 to 300 $\mu$m;

a drug impregnating the porous ceramic via the pores; and a surface layer for controlling the release of the drug, the surface layer being formed to cover at least a portion of the outer surface of the porous ceramic and having a porosity lower than that of the porous ceramic.

In the present invention, the drug used to impregnate the porous ceramic is not limited; in other words, any drug can be used, depending on the disease to be treated.

In the present invention, the drug release period and concentration (especially the drug release concentration immediately after the ceramic is embedded) can be controlled by adjusting the area, the pore size, the film thickness, and the like of the surface layer formed to cover the porous ceramic. Preferably, the pore size of the surface layer should be less than 10 $\mu$m, and its film thickness 300 $\mu$m or less.

The second object of the present invention is achieved by using, as the above porous ceramic and surface layer, a substance which can decompose within a living body. The porous ceramic is preferably not only decomposable but also absorbable in a living body. An example of the preferred porous ceramic is formed of calcium phosphate compounds having Ca/P ratio of 1.45–1.55. When the Ca/P ratio of the calcium phosphate compounds is not within the above range, it tends to produce hydroxy apatite which hardly absorbed by living body after decomposition. More preferably, the porous ceramic is formed of tricalcium phosphate (TCP) which decomposes and is absorbed by a living body. As the surface layer decomposable in a living body, collagen which is decomposed and absorbed by a living body and has high affinity to a living body can be used in addition to the ceramic such as TCP decomposable in a living body.

When the above porous ceramic and surface layer decomposable in a living body are used, as a drug impregnated in the porous ceramic is gradually released, the porous ceramic itself is gradually decomposed from its surface and absorbed in or discharged from a living body. Therefore, since pores gradually become shallow, drug components impregnated deep in the pores can be easily released. In addition, no unnecessary alien substance remains in a living body because the porous ceramic is finally decomposed and disappears.

BRIEF DESCRIPTION OF THE DRAWINGS

FIG. 1 is a sectional view showing a structure of a drug-impregnated ceramic according to an embodiment of the present invention;

FIG. 2 is a sectional view showing a structure of a drug-impregnated ceramic according to another embodiment of the present invention; and FIG. 3 is a perspective view showing a mold for preparing the drug-impregnated ceramic shown in FIG. 1.

DETAILED DESCRIPTION OF THE PREFERRED EMBODIMENT

A first embodiment of the present invention will be described below with reference to FIGS. 1 to 3. FIG. 1 is a sectional view showing a structure of a drug-impregnated ceramic according to the first embodiment. As shown in FIG. 1, drug-impregnated ceramic 1 is spherical and has an outer diameter of about 5 mm. Referring to FIG. 1, reference numeral 2 denotes a porous ceramic. Porous ceramic 2 has pores 3 communicating with its outer surface and having a pore size of 10 to 300 μm. A drug (not shown) such as an antibiotic is impregnated in pores 3. The surface of ceramic 2 is covered with surface layer 4. Layer 4 has film thickness of 100 μm and pores having a pore size of 10 μm or less. Drug injection port 5 is formed in part of layer 4 to impregnate a drug in ceramic 2.

The drug-impregnated ceramic according to the first embodiment may have a structure shown in FIG. 2. This embodiment is identical to the embodiment shown in FIG. 1 except that its shape is columnar, and the same reference numerals as in FIG. 1 denote the same parts in FIG. 2.

In this embodiment, either of porous ceramic 2 and surface layer 4 consists of tricalcium phosphate (TCP) which can be decomposed and absorbed by a living body, especially low-temperature β-TCP. TCP includes high-temperature α-TCP in addition to β-TCP. In this case low-temperature β-TCP is used because α-TCP is decomposed too fast and tends to produce hydroxy apatite which is hardly absorbed by a living body after decomposition.

Preparation of drug-impregnated ceramic 1 according to the above embodiments will be described below.

Formation of Ceramic Capsule Comprising Porous Ceramic 2 and Surface Layer 4

15 ml of water and 15 ml of a polyacrylate surfactant as a foam stabilizer for maintaining foams were added and mixed to 30 g of a β-TCP powder synthesized by a mechanochemical method. 3 g of a nonylphenol surfactant as a foaming agent for making foams were added and stirred to satisfactorily foam the mixture. The resultant foamed slurry was injected into injection port 7 of gypsum or paraffin mold 6 having spherical molding chambers 8 as shown in FIG. 3. The injected slurry was dried at 40° to 50° C. for one day or more and then removed from the mold and sintered. Sintering was performed at a heating rate of 100° C./hr. When a sintering temperature reached 1,100° to 1,150° C., sintering was kept at this temperature for one hour, after which stopped sintering and gradually cooled the resultant material. In this manner, spherical porous ceramic 2 covered with surface layer 4 was prepared.

Shape determination of ceramic 2, and control of a pore size, porosity, a thickness of layer 4 and the like are performed as follows.

(1) Shape Determination

Following the same procedures as described above, not only a spherical drug-impregnated ceramic as shown in FIG. 1, but also drug-impregnated ceramics having various shapes such as a columnar one as shown in FIG. 2 can be prepared. That is, porous ceramic 2 having an arbitrary shape can be prepared by arbitrarily setting the shape of the molding cavity of mold 6.

(2) Control of Porosity and Pore Size

The porosity and pore size are controlled by variously changing a ratio between the foaming agent, water, and the foam stabilizer. Table 1 below shows porous ceramic 2 prepared by changing a ratio between these components and porosity and pore size obtained in this ceramic.

TABLE 1

|  |  | Example 1 | Example 2 | Example 3 |
|---|---|---|---|---|
| β-TCP | (g) | 30 | 30 | 30 |
| Forming Agent | (ml) | 1.5 | 3.0 | 3.0 |
| Water | (ml) | 15 | 14 | 16 |
| Foam Stabilizer | (ml) | 2 | 6 | 15 |
| Porosity | (%) | 30 | 50 | 70 |
| Pore Size (μm) (or less) |  | 150 | 200 | 300 |

As shown in Table 1, with the composition of Examples 1, a porous ceramic having a porosity of 30% and a pore size of 150 μm or less was prepared. With the composition of Example 2, a porous ceramic having a porosity of 50% and a pore size of 200 μm or less was prepared. With the composition of Example 3, a porous ceramic having a porosity of 70% and a pore size of 300 μm or less was prepared. In this manner, by changing the ratio between the respective materials, porous ceramic 2 having an arbitrary porosity and pore size can be prepared.

(3) Control of Film Thickness of Surface Layer 4

Porous ceramic 2 injected in the mold, dried therein, and then removed therefrom already has surface layer 4 having a thickness of 50 to 100 μm. Layer 4 has only a small number of pores having a pore size of less than 10 μm. Such layer 4 is formed because bubbles tend to disappear on a contact surface between the slurry and the mold, thereby interfering with foam formation. In order to increase the film thickness of layer 4, a non-foamed slurry of β-TCP may be coated on the surface of porous ceramic 2 prepared by sintering described above. After the coated slurry is dried, the resultant material is sintered again at a sintering temperature of 1,050° to 1,100° C. for one to two hours to form surface layer 4.

Impregnation of Drug

An antibiotic was impregnated as follows in a ceramic capsule for drug impregnation prepared following the same procedures as described above and having an outer diameter of 5 mm, a size of pores 3 of 200 μm, and a film thickness of surface layer 4 of 100 μm. That is, drug injection port 5 was formed in layer 4. Subsequently, an antibiotic solution was impregnated from port 5 into ceramic 2, and then the entire ceramic capsule was dipped in the antibiotic solution.

An effect of drug-impregnated ceramic 1 prepared as described above was checked as follows. That is, ceramic 1 was embedded in femurs of rabbits, and the antibiotic concentrations in the femurs were periodically measured. As a result, the antibiotic concentration in a bone marrow was not significantly high immediately after ceramic 1 was embedded and was substantially constant from immediately after ceramic 1 was embedded to the end of release. In addition, it was confirmed that the antibiotic was continuously released at a predetermined concentration for three to four weeks by one capsule. Also, it was confirmed that bone formation around the embedded portion was very good and β-TCP ceramic was decomposed and absorbed to reliably replaced by bones.

A second embodiment of the present invention will be described below. This embodiment is identical to the first embodiment in its shape and the like except that surface layer 4 of a ceramic capsule was formed of collagen. Following the same procedures as in the first embodiment, an antibiotic was impregnated in the ceramic capsule, and the entire capsule was dipped in the antibiotic. The resultant drug-impregnated ceramic was embedded in femurs of rabbits, and the antibiotic concentrations in the femurs were periodically measured. As a result, as in the above first embodiment, the antibiotic concentration in the femurs was constant. In addition, it was confirmed that the antibiotic was continuously released for about four weeks by one capsule. Also, substantially the same effect as that of the first embodiment was obtained. Moreover, since surface layer 4 was formed of collagen, the affinity to a living body of the drug-impregnated ceramic was further improved when it is embedded in a living body.

A third embodiment of the present invention will be described below. This embodiment was identical to the above embodiments in its shape and the like except that porous ceramic 2 of a ceramic capsule was formed of a mixture of β-TCP and α-TCP. Following the same procedures as in the above embodiments, an antibiotic was impregnated in the ceramic capsule, and then the entire ceramic capsule was dipped in the antibiotic. The resultant drug-impregnated ceramic was embedded in femurs of rabbits, and the antibiotic concentrations in the femurs were periodically measured. As a result, as in the above first embodiment, the antibiotic concentration in the femurs was constant. In addition, it was confirmed that antibiotic was continuously released for about two to three weeks by one capsule.

As described above, since porous ceramic 2 of the third embodiment contains α-TCP having a high decomposition rate, a drug release period is shortened. Since ceramic 2 is decomposed fast, however, another effect of promoting bone replacement with respect to a surrounding portion is obtained.

In each of the above first to third embodiments, the surface layer is formed to cover the entire porous ceramic. The surface layer, however, need not cover the entire ceramic. That is, the surface layer may be formed to cover only a portion of the ceramic as long as release of a drug can be controlled for only a predetermined period after the ceramic is embedded.

Moreover, the present invention can be changed or modified without departing from the spirit and scope of the invention.

As has been described above, according to the present invention, a surface layer for controlling release of drug is formed to cover the surface of the drug-impregnated porous ceramic. By adjusting the area, film thickness, pore size and the like of the surface layer, it is possible to control a period, concentration and the like of the drug to be released into an affected part. In particular, by controlling release of the drug immediately after the ceramic is embedded, the drug can be reliably released at a substantially constant concentration throughout a long time period from immediately after the ceramic is embedded to the end of release.

In addition, since the embedded ceramic itself is decomposed and absorbed by a living body, there is provided a drug-impregnated ceramic which need not be removed from a living body even after a drug is completely released.

What is claimed is:

1. In a drug-impregnated ceramic which is to be embedded in a living body for release of the drug impregnated therein, into the body, the improvement wherein said drug-impregnated ceramic comprises:
   a porous ceramic having pores with a pore size of 10 to 300 μm, said drug being impregnated into said pores; and
   a means to control the release of sad drug from the pores of said porous ceramic comprising a surface layer covering at least a portion of the outer surface layer of said porous ceramic and having a pore size smaller than that of said porous ceramic to control release of the drug from the pores of the porous ceramic.

2. The ceramic according to claim 1, wherein said surface layer has pores with a pore size of less than 10 μm and a film thickness of not more than 300 μm.

3. The ceramic according to claim 1, wherein said porous ceramic and said surface layer can decompose within a living body.

4. The ceramic according to claim 3, wherein said porous ceramic comprises a calcium phosphate compound having a Ca/P ratio of 1.45–1.55.

5. The ceramic according to claim 3, wherein said porous ceramic consists of tricalcium phosphate.

6. The ceramic according to claim 3, wherein said surface layer consists of tricalcium phosphate having pores with a pore size of less than 10 μm and a film thickness of not more than 300 μm.

7. The ceramic according to claim 3, wherein said surface layer consists of collagen having pores with a pore size of not more than 10 μm and a film thickness of not more than 300 μm.

8. The ceramic according to claim 1, wherein said surface layer is formed of porous ceramic material which can decompose within a living body.

9. The ceramic according to claim 8, wherein the porous ceramic material of the surface layer has the same composition as the porous ceramic.

10. The ceramic according to claim 3, wherein said surface layer is formed of porous ceramic material which can decompose within a living body.

11. The ceramic according to claim 10, wherein the porous ceramic material of the surface layer has the same composition as the porous ceramic.

12. The ceramic according to claim 11, wherein said porous ceramic layer and said porous ceramic material comprise a calcium phosphate compound having a Ca/P ratio of 1.45–1.55.

13. The ceramic according to claim 11, wherein said porous ceramic layer and said porous ceramic material consists of tricalcium phosphate.

14. The ceramic according to claim 11, wherein said surface layer consists of tricalcium phosphate having pores with a pore size of less than 10 μm and a film thickness of not more than 300 μm.

15. The ceramic according to claim 11, wherein the surface layer is in contact with only the outer surface of said porous ceramic and covers the entire outer surface of said porous ceramic except for a drug injection port.

16. The drug-impregnated ceramic of claim 1 wherein the porosity of the porous ceramic is 30 to 70% and the pore size is equal to or greater than 150 μm.

17. The drug-impregnated ceramic of claim 16 wherein the surface layer is 4 to 300 μm thick and has a pore size of the up to 10 μm.

18. The drug-impregnated ceramic of claim 1 wherein the drug is an antibiotic.

19. The drug-impregnated ceramic of claim 12 wherein the drug is an antibiotic.

* * * * *